United States Patent
Bedekar et al.

(10) Patent No.: US 6,956,142 B2
(45) Date of Patent: Oct. 18, 2005

(54) PROCESS FOR ECO-FRIENDLY SYNTHESIS OF BROMOBENZENE

(75) Inventors: Ashutosh Vasant Bedekar, Bhavnagar (IN); Kumar Pushpito Ghosh, Bhavnagar (IN); Subbarayyappa Adimurthy, Bhavnagar (IN); Gadde Ramachandraiah, Bhavnagar (IN)

(73) Assignee: Central Salt and Marine Chemicals Research Institute, Bhavnagar (IN)

( * ) Notice: Subject to any disclaimer, the term of this patent is extended or adjusted under 35 U.S.C. 154(b) by 126 days.

(21) Appl. No.: 10/739,756

(22) Filed: Dec. 17, 2003

(65) Prior Publication Data

US 2005/0137431 A1    Jun. 23, 2005

(51) Int. Cl.$^7$ .................... C07C 17/02; C07C 17/013
(52) U.S. Cl. .................... 570/206; 570/190; 570/201
(58) Field of Search .................... 570/206, 190, 570/201

(56) References Cited

U.S. PATENT DOCUMENTS 3,622,640 A * 11/1971 Taylor et al. ............... 570/206
4,855,517 A *  8/1989 Metz et al. ................. 570/206

* cited by examiner

Primary Examiner—Elvis O. Price
(74) Attorney, Agent, or Firm—Rutan & Tucker, LLP

(57) ABSTRACT

A new eco-friendly process is described in the present invention for the preparation of bromobenzene through substitution of one of the C—H proton of benzene ring with a highly reactive hypobromous acid generated in situ, said process comprises the steps of activating a water soluble, easy to handle, brominating reagent with a mineral acid at elevated temperature and atmospheric pressure to generate active bromine species which in turn reacts with benzene.

17 Claims, No Drawings

PROCESS FOR ECO-FRIENDLY SYNTHESIS OF BROMOBENZENE

FIELD OF THE INVENTION

The present invention relates to a process for eco-friendly synthesis of bromobenzene through in situ hypobromite generation.

BACKGROUND OF THE INVENTION

Bromobenzene is widely used as an additive in motor oils and as a heavy liquid solvent especially where mass crystallization is required. Further, it is used as a starting material in several organic syntheses, especially in the preparation of organometallic reagents such as phenyl magnesium bromide, phenyl lithium and diphenyl zinc which in turn are employed in the preparative synthesis involving carbon-carbon bond formations.

Reference may be made to PCT-international application No 88,07,513 to M. Rule et al. wherein an improved vapor phase bromination of aromatic compounds was disclosed. The reaction was carried out in the presence of oxygen and an iron containing silica-alumina catalyst at 351° C. Hydrobromic acid was used as a bromine source. The conversion of aromatic compound (substrate) to the desired bromo compound was only 60 percent. The drawbacks of this method are that the experimental temperature is too high and the brominating agent via hydrobromic acid is highly corrosive even at room temperatures. Moreover, this method requires a catalyst and the yields are only 60%. Conducting the vapor phase reaction at high temperatures particularly with hydrocarbons in the presence of oxygen is highly hazardous and risky.

The paper entitled Molecular sieves as catalyst for aromatic bromination in *Zeolite* 1987, 7(6), 499 by J. Zabicky, et al discloses the ring bromination of aromatic substrates using liquid bromine as brominating agent and in the presence of mordenite and 13X type zeolite containing metallic iron under reflux temperature. Quantitative yields of p- and o-bromoderivatives were obtained when the reaction was carried out in the absence of sunlight. The main limitations of this method are that the reaction should be carried out in sun light to avoid the formation of dibromo derivatives. Hazardous liquid bromine is the brominating agent which requires special handling precautions and equipment. The requirement of mordenite and 13X type zeolite containing metallic iron is essential for ensuring the product formation. Moreover the bromination of benzene is incomplete even at reflux temperature when sun light is absent. The Japanese patent, JP 6293,242 to H. Ishida et al discloses the preparation of p dibromobenzene by oxidative bromination of benzene using liquid bromine and/or hydrobromic acid as brominating agents. The reaction was carried out in a gaseous phase at 200° C. in presence of oxygen. In this reaction the rate of reaction was increased by the use of sodium zeolite containing 18 percent copper. The draw backs of this method are that the reaction should be conducted in gaseous phase at 200° C. in the presence of oxygen. Sodium supported zeolite containing 18% copper ions is required to catalyze the reaction. It gives 95% dibromobenzene and negligible quantity of bromobenzene with 45% conversion. Moreover, the brominating reagents used here are very corrosive, toxic and need special skills and equipment to handle them.

A paper entitled "Oxidative bromination of aromatic compounds catalysed by the hetero poly acids" in *Kinet.* *Catal.* 1982, 23(4), 992 by T. V. Gorodeestsaya, describes the use of a hetero poly acids containing molybdenum and vanadium to catalyze the reaction by hydrobromic acid and oxygen in aqueous acetic acid. The hetero poly-acid catalyzes the oxidation of bromide ions by oxygen to form bromine which was further used in the ring substitution reactions of aromatic compounds. The drawbacks of this method are that the experimental temperature is too high and the brominating agent, hydrobromic acid is highly corrosive even at room temperatures. Moreover, this method requires a catalyst and the yields are only 60%. Conducting the vapor phase reaction at high temperatures particularly hydrocarbons in the presence of oxygen is highly hazardous and risky.

The Japanese patent JP 7,762,201 to Y. Toteraishi, et al discloses the process of bromination of organic compounds using liquid bromine. The byproduct hydrobromic acid produced in the reaction was oxidized using chlorine gas which was further used up to complete the bromination reaction. The drawbacks of this process are that it requires highly toxic and corrosive liquid bromine as brominating and chlorine as oxidizing agents which require special apparatus and operation skills.

The patent, JP 7616,620 to T. Asai et al discloses the preparation of hexabromobenzene having high melting point. In this process benzene was directly added to mixture of liquid bromine and anhydrous aluminium chloride maintained at 40° C. and the entire mixture stirred for four hours. Water was added and the temperature was raised to 70° C. to remove bromine. Finally the pH of the solution was adjusted to 9 with sodium carbonate solution to obtain 97% hexabromobenzene having melting point 325° C. In this method it was possible to obtain only hexabromobenzene and not bromobenzene. The draw back of this method is that it involves a neutralization step and precautionary measures to handle corrosive and hazardous liquid bromine. Further, this method requires anhydrous aluminium chloride as catalyst which unnecessarily increases process steps and thus effect the production cost.

The Japanese patent JP 7420,126 to T. Komiyama, et al discloses the bromination of aromatic hydrocarbons containing either halo or carboxyl group by treatment with liquid bromine in the presence of aqueous solution of ferric bromide under 5 $kg/cm^2$ nitrogen pressure. Then, the pressure was raised to 30 $kg/cm^2$ with oxygen and the reaction mixture was heated to 200° C. for one hour. The drawback of this method are that it employs liquid bromine, which is hazardous and corrosive. Beside the reaction is carried out at a very high pressure and temperature which is cost effective.

In Japanese patent JP 7436,633, to T. Komiyama, et al disclose the preparation of bromobenzene by the reaction of benzene with ammonium bromide in the presence of support material containing copper bromide. In this process, benzene-ammonium bromide-steam-air in definite volume percent was passed through the catalyst at 300° C. with contact time of 2.5 seconds. The drawbacks of this method are that it is a vapor phase reaction and reaction temperature is too high. Moreover, conducting this vapor phase reaction at high temperatures particularly with hydrocarbons in the presence of oxygen is highly hazardous and risky. Maintaining the steam to air in definite volume percent is also difficult.

O. A. Sadygor et al in USSR patent SU 1,468,896 have disclosed the preparation of bromobenzene in high yield. In this process, the bromination of benzene was carried out at 20–40° C. with 1–1.3 mole equiv of sodium bromide or potassium bromide in the presence of 1–1.3 mole equiv of sodium hypochlorite in an acidic medium containing either 15–36.5% aqueous hydrochloric acid or 15–96% aqueous sulphuric acid. The reaction mixture was aged for 3–5 hours at 20–40° C. The main limitation of this method is that the maximum concentration of hypochlorite solution available is 4%, as a result large containers are required to handle large volumes hypochlorite solutions in large scale production of bromobenzene.

OBJECTS OF THE INVENTION

The main object of the present invention is to provide a process for eco-friendly synthesis of bromobenzene which obviates the drawbacks as detailed above.

Another object of the present invention is to dispense the use of solid catalyst and liquid bromine in the preparation of bromobenzene.

Yet another object of the present invention is to have high atomic substitution of bromine on aromatic substrates in aqueous phase reaction.

Yet another object of the present invention is to use a water soluble and non-hazardous solid brominating reagent having bromide and bromate ions ratio in the range of 1.8:1 to 2.2:1 for bromination process.

Yet another object of the present invention is to use very small quantity of phase-transfer catalyst for uniform mixing of organic and aqueous layer.

Still another object of the present invention is to prepare bromobenzene at reflux benzene temperature and obviate the need of high temperature and autogeneous pressure.

Still another object of the present invention is to prepare colorless bromobenzene having boiling point of 154–156° C.

SUMMARY OF THE INVENTION

A new eco-friendly process is described in the present invention for the preparation of bromobenzene through substitution of one of the C—H proton of benzene ring with a highly reactive hypobromous acid generated in situ, said process comprises the steps of activating a water soluble, easy to handle, brominating reagent with a mineral acid at elevated temperature and atmospheric pressure to generate active bromine species which in turn reacts with benzene. The compound bromobenzene thus obtained is useful in the preparation of organomettalic reagents such as phenyl magnesium bromide, phenyl lithium and diphenyl zinc etc.

DETAILED DESCRIPTION OF THE INVENTION

Accordingly, the present invention provides a process for eco-friendly synthesis of bromobenzene which comprises the steps of:

(i) dissolving about 200 to 400 grams of a brominating reagent containing about 35 to 45% wt/wt of active bromine per liter of water to obtain an aqueous solution;
(ii) adding about 2 to 10 mole equivalents of benzene per atom of bromine to the aqueous solution of step (i);
(iii) adding a surfactant to the mixture of step (ii) under constant stirring;
(iv) refluxing the reaction mixture of step (iii) at temperature in the range of about 50 to 80° C.;
(v) adding a mineral acid in the concentration range of about 3 to 4 equivalents per atom of bromine to the refluxed reaction mixture of step (iv);
(vi) stirring the mixture of step (v) for a time period in the range of about 20 to 48 hours at elevated temperatures;
(vii) cooling the mixture of step (vi) and separating the same into an organic layer and an aqueous layer;
(viii) extracting the aqueous layer of step (vii) with an organic solvent;
(ix) combining the extracts of the organic layers and washing the layers successively with water and brine;
(x) drying the organic layer of step (ix) over anhydrous sodium sulfate, and
(xi) stripping off the organic solvent to obtain crude product and distilling the crude product to obtain clear and colorless bromobenzene.

In an embodiment of the present invention wherein in step (i), the brominating reagent used contains about 40% wt/wt of active bromine.

In another embodiment of the present invention wherein in step (i), the brominating agent used has bromide to bromate ratio in the range of about 1.8:1 to about 2.2:1.

In yet another embodiment of the present invention wherein in step (iii), the surfactant used is sodium lauryl sulfate.

In still another embodiment of the present invention wherein in step (iv), the reaction mixture is refluxed using water condenser.

In one more embodiment of the present invention wherein in step (v), the mineral acid used is selected from sulfuric acid, hydrochloric acid and perchloric acid.

In one another embodiment of the present invention wherein in step (v), the mineral acid is added to the refluxed reaction mixture at the rate of about 1.5 to 4.0 m/hour.

In a further embodiment of the present invention, the sulfuric acid added is about 50% aqueous sulfuric acid.

In a further more embodiment of the present invention, the hydrochloric acid added is about 35% aqueous hydrochloric acid.

In an embodiment of the present invention, the perchloric acid added is about 70% aqueous perchloric acid.

In another embodiment of the present invention wherein in step (vi), the mixture is heated at temperatures ranging between 50 to 80° C.

In yet another embodiment of the present invention wherein in step (vii), the mixture is cooled to room temperature and separated into an organic layer and an aqueous layer.

In still another embodiment of the present invention wherein in step (viii), the organic solvent used is selected from the group comprising of ether, dichloromethane, dichloroethane, ethyl acetate, petroleum ether and benzene.

In one more embodiment of the present invention wherein in step (xi), the organic solvent is stripped off at reduced pressure.

In one another embodiment of the present invention wherein in step (xi), the crude product is distilled under vacuum.

In a further embodiment of the present invention, the bromobenzene thus obtained has boiling point in the range of 154–156° C.

In a further more embodiment of the present invention, the yield of bromobenzene obtained is in the range of 50 to 90%.

According to the present invention, the brominating reagent react with the protons and produce hypobromous acid in solution.

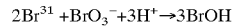

$$2Br^{31} + BrO_3^- + 3H^+ \rightarrow 3BrOH$$

The electrophilic bromine in BrOH attacks the benzene ring and form bromo benzene by replacing one of the C—H proton through substitution mechanism.

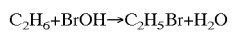

The reaction was conducted on a laboratory scale in 500 ml three neck round bottom flak fitted with an efficient water condenser. A water soluble brominating reagent having bromide to bromate mole ratio 2:1 was used as a source of bromine. The requisite hypobromous acid (BrOH) was generated in situ by slow addition of three equivalents of a mineral acid such as sulfuric acid, hydrochloric acid or perchloric acid and allowed to react with excess benzene at elevated/reflux temperature under constant stirring to yield the desired product, bromobenzene.

The dissolution of solid brominating reagent in deionized water in the concentration range of 15 to 50%, preferably in the range of 20 to 40% is sufficient for effective bromination for substitution reaction. Dilution below 20% will only lead to excess of water and will take longer time to reach the boiling point of benzene. The process will become energy intensive. Dilution above 40% and at temperature above 70° C. in presence of small quantity of excess acid may cause for the disproportionation of hypobromous acid to volatile bromine and bromate ion. This would result in lowering the product yield.

In the preferred invention, the temperature of the reaction mixture may be maintained in the temperature range of 40 to 95° C., preferably in the range of 50 to 80° C. The bromination reaction proceeds through substitution reaction at normal to boiling temperature of benzene and atmospheric pressure. At temperature below 40° C., the bromination reaction is very slow and the bromobenzene obtained after 48 hours reaction was only ca 50%. Gradual increase of the temperature to ca 65° C. helps in enhancing the yield of bromobenzene to ca 75% and further increasing the temperature to boiling temperature of benzene yields about 90% bromobenzene in the stipulated time period. In accordance with the present invention the addition of acid plays a very vital role in activating the brominating reagent. The acid may be added to the reaction mixture at the rate in the range of 1 to 10 ml per hour, preferably in the range of 2 to 7 ml per hour. The faster rate of addition of acid will disproportionate the hypobromous acid produced in situ to elementary bromine and bromate ions. The addition rate less than 1 ml per hour will have no advantage, on the contrary, increases the total time of reaction. With the use of perchloric acid the yield is less than 50%, which adversely affect the economics of the process. Besides, special care has to be taken, as perchloric acid is explosive in nature at high temperature. The use of sulphuric acid helps in maximum yield of bromobenzene. In carrying out the present invention, wherein maximum substitution of bromine is to be achieved, the reaction period may be varied in the range of 6 to 60 hours, preferably in the range of 10 to 50 hours. Decreasing the reaction time to less than 10 hours, lowers the yield of bromobenzene which may turn out to be uneconomical. Increasing the reaction time beyond 50 hours, no advantage is accrued.

In the preferred embodiment of the present invention, optimum quantity of phase transfer catalyst is essential. For laboratory scale batch of 10 to 100 grams bromobenzene, the phase transfer catalyst may be added in the range of 0.1 to 0.5 grams. The use of phase transfer catalyst should be increased for scale up preparation of bromobenzene. This catalyst helps in uniform mixing of the organic layer with aqueous layer and this in turn helps in replacing one of the C—H protons for bromine atom through substitution reaction. Therefore the quantity of phase transfer catalyst plays a very significant role in obtaining higher yield of bromobenzene.

In the present invention it was observed that equivalent quantity of benzene per atom of bromine assist in higher yields of bromobenzene. Therefore, 1 to 20 equivalent of benzene per atom of bromine, preferably in the range of 2 to 15 equivalent of benzene per atom of bromine was added to the reaction mixture as described earlier. The addition of less than 2 equivalent of benzene resulted in lower yields of bromobenzene and more than 15 equivalent of benzene resulted in excess of unreacted benzene which needs to be recovered from organic layer and subsequently separated from the bromobenzene.

The process according to the present invention was carried out by generating hypobromous acid with the action of a mineral acid on brominating reagent having a mixture of sodium bromide and sodium bromate at elevated temperature between 50 and 80° C. and allowing to react with excess benzene in the presence of phase transfer catalyst. Mineral acids such as sulfuric, hydrochloric and perchloric acids were used. High yields of bromobenzene were obtained when sulfuric acid and five or more equivalents of benzene per atom of bromine were used in the reaction. The bromination reaction occurs in solution state at normal at boiling temperature (50–80° C.) of benzene and atmospheric pressure. Loss of hypobromous acid in the form of volatile bromine and formation of dibromobenzene were negligible in this reaction. The product, bromobenzene was identified and characterized by GC and $^1$H-NMR analysis after comparison with an authentic sample.

The inventive steps of the present invention are (i) bromobenzene can be prepared in a single step from a water soluble brominating reagent containing active bromine and it dispenses the use of hazardous liquid bromine as brominating reagent;

(ii) in the bromination reaction, benzene itself acts as a solvent for the reaction and it does not require any other solvent for dispersion;

(iii) the in situ generated hyphobromous acid, reacts directly with benzene ring by replacing one of the C—H protons through substitution and thus obviates the need of any metal based catalyst to enhance the bromination reaction;

(iv) the liquid phase bromination reaction in the temperature range 50 to 80° C. gave about 90% bromobenzene, thereby the hazardous vapor phase bromination at high temperature in the presence of catalyst can be avoided;

(v) the bromination reaction in solution phase at reflux benzene temperature and atmospheric pressure gave bromobenzene with high yields and atom efficiency and thereby avoiding high pressure bromination reaction; and (vi) the substitution of bromine on the benzene ring take place without the use of any oxidising agent.

The following examples are given by way of illustrations of the present invention and should not be construed to limit the scope of the present invention.

EXAMPLE 1

29.1 g of brominating reagent was dissolved in 75 ml water taken in 500 ml three neck round bottom flask fitted with an water condenser. To it, 5 equivalents (57 ml, 0.73 mol) of benzene per atom of bromine and 0.1 g of sodium lauryl sulfate were added and then the flask was slowly heated to 70° C. under stirring. A solution of 16.4 ml (50%) sulfuric acid (0.15 mol) was added to the hot reaction mixture over a period for 10 hours. The mixture was stirred for another 30 h at 70° C. and then cooled to room temperature. The organic and aqueous layers were separated. The aqueous layer was extracted at least three times with minimum quantity of ether. The extracts were combined with the organic layer, washed successively with water and brine and dried over anhydrous sodium sulfate. Solvent was stripped at reduced pressure to get crude product which was purified by vacuum distillation to give 20 g or 87.5% of clear and colorless liquid bromo benzene having boiling point 154–156° C.

EXAMPLE 2

116.4 g of brominating reagent was dissolved in 300 ml water taken in 1000 ml three neck round bottom flask fitted with an water condenser. To it, 5 equivalents (228 ml, 2.92 mol) of benzene per atom of bromine and 0.4 g of sodium lauryl sulfate were added and then the flask was slowly heated to 70° C. under stirring. A solution of 65.6 ml (50%) sulfuric acid (0.60 mol) was added to the hot reaction mixture over 10 hours. The mixture was stirred for another 30 h at 70° C. and then cooled to room temperature. The organic and aqueous layers were separated. The aqueous layer was extracted at least three times with minimum quantity of ether. The extracts were combined with the organic layer, washed successively with water and brine and dried over anhydrous sodium sulfate. Solvent was stripped at reduced pressure to get crude product which was purified by vacuum distillation to give 82 g or 89.7% of clear and colorless liquid bromo benzene having boiling point 154–156° C.

EXAMPLE 3

29.10 g of brominating reagent was dissolved in 75 ml water taken in 500 ml three neck round bottom flask fitted with water condenser. To it, 5 equivalents (57 ml, 0.73 mol) of benzene per atom of bromine and 0.1 g of sodium lauryl sulfate were added and then the flask was slowly heated to 70° C. under stirring. A solution of 15.5 ml (35%) hydrochloric acid (0.15 mol) was added to the hot reaction mixture over 10 hours. The mixture was stirred for another 30 h at 70° C. and then cooled to room temperature. The organic and aqueous layers were separated. The aqueous layer was extracted at least three times with minimum quantity of ether. The extracts were combined with the organic layer, washed successively with water and brine and dried over anhydrous sodium sulfate. Solvent was stripped at reduced pressure to get crude product which was purified by vacuum distillation to give 18.6 g or 81.3% of clear and colorless liquid bromo benzene having boiling point 154–156° C.

EXAMPLE 4

29.10 g of brominating reagent was dissolved in 75 ml water taken in 500 ml three neck round bottom flask fitted with water condenser. To it, 2 equivalents (22.8 ml, 0.292 mol) of benzene per atom of bromine and 0.1 g of sodium lauryl sulfate were added and then the flask was slowly heated to 70° C. under stirring. A solution of 16.4 ml (50%) sulfuric acid (0.15 mol) was added to the hot reaction mixture over 8 hours. The mixture was stirred for another 25 h at 80° C. and then cooled to room temperature. The organic and aqueous layers were separated. The aqueous layer was extracted at least three times with minimum quantity of ether. The extracts were combined with the organic layer, washed successively with water and brine and dried over anhydrous sodium sulfate. Solvent was stripped at reduced pressure to get crude product which was purified by vacuum distillation to give 11.9 g or 52.3% of clear and colorless liquid bromo benzene having boiling point 154–156° C.

EXAMPLE 5

29.10 g of brominating reagent was dissolved in 75 ml water taken in 500 ml three neck round bottom flask fitted with water condenser. To it, 5 equivalents (57 ml, 0.73 mol) of benzene per atom of bromine and 0.1 g of sodium lauryl sulfate were added and then the flask was slowly heated to 80° C. under stirring. A solution of 22 ml (70%) perchloric acid (0.15 mol) was added to the hot reaction mixture over 10 hours. The mixture was stirred for another 30 h at 80° C. and then cooled to room temperature. The organic and aqueous layers were separated. The aqueous layer was extracted at least three times with minimum quantity of ether. The extracts were combined with the organic layer, washed successively with water and brine and dried over anhydrous sodium sulfate. Solvent was stripped at reduced pressure to get crude product which was purified by vacuum distillation to give 10.7 g or 53.5% of clear and colorless liquid bromo benzene having boiling point 154–156° C.

The main advantages of the present invention are
1. This process is easy, eco-friendly and less energetic compared to hitherto known processes.
2. The process requires a simple and solid brominating reagent for the in situ generation of reactive species which subsequently is utilized in the bromination of benzene,
3. The brominating reagent is solid and non-hazardous and it does not require any special equipment or handling skills,
4. The reaction occurs in solution at the boiling temperature of benzene and atmospheric pressure,
5. The process operates under ambient conditions of temperature and pressure,
6. The reaction yields negligible quantities of poly bromo compounds,
7. The reaction does not require any metal-based catalysts,
8. The brominating reagent can easily be obtained at reduced cost from one of the intermediate products in the bromine recovery process,
9. The bromination reaction has high yields and atom efficiency.
10. The byproducts left out in aqueous phase are simple inorganic salts and can be discharged safely.

What is claimed is:
1. A process for eco-friendly synthesis of bromobenzene which comprises the steps of:
  (i) dissolving about 200 to 400 grams of a brominating reagent containing about 35 to 45% wt/wt of active bromine per liter of water to obtain an aqueous solution;
  (ii) adding about 2 to 10 mole equivalents of benzene per atom of bromine to the aqueous solution of step (i);
  (iii) adding a surfactant to the mixture of step (ii) under constant stirring;
  (iv) refluxing the reaction mixture of step (iii) at temperature in the range of about 50 to 80° C.;
  (v) adding a mineral acid in the concentration range of about 3 to 4 equivalents per atom of bromine to the refluxed reaction mixture of step (iv);
  (vi) stirring the mixture of step (v) for a time period in the range of about 20 to 48 hours at elevated temperatures;

(vii) cooling the mixture of step (vi) and separating the same into an organic layer and an aqueous layer;

(viii) extracting the aqueous layer of step (vii) with an organic solvent;

(ix) combining the extracts of the organic layers and washing the layers successively with water and brine;

(x) drying the organic layer of step (ix) over anhydrous sodium sulfate, and (xi) stripping off the organic solvent to obtain crude product and distilling the crude product to obtain clear and colorless bromobenzene.

2. A process as claimed in claim 1 wherein in step (i), the brominating reagent used contains about 40% wt/wt of active bromine.

3. A process as claimed in claim 1 wherein in step (i), the brominating agent used has bromide to bromate ratio in the range of about 1.8:1 to about 2.2:1.

4. A process as claimed in claim 1 wherein in step (iii), the surfactant used is sodium lauryl sulfate.

5. A process as claimed in claim 1 wherein in step (iv), the reaction mixture is refluxed using water condenser.

6. A process as claimed in claim 1 wherein in step (v), the mineral acid used is selected from sulfuric acid, hydrochloric acid and perchloric acid.

7. A process as claimed in claim 1 wherein in step (v), the mineral acid is added to the refluxed reaction mixture at the rate of about 1.5 to 4.0 m/hour.

8. A process as claimed in claim 7, wherein the sulfuric acid added is about 50% aqueous sulfuric acid.

9. A process as claimed in claim 7, wherein the hydrochloric acid added is about 35% aqueous hydrochloric acid.

10. A process as claimed in claim 7, wherein the perchloric acid added is about 70% aqueous perchloric acid.

11. A process as claimed in claim 1 wherein in step (vi), the mixture is heated at temperatures ranging between 50 to 80° C.

12. A process as claimed in claim 1 wherein in step (vii), the mixture is cooled to room temperature and separated into an organic layer and an aqueous layer.

13. A process as claimed in claim 1 wherein in step (viii), the organic solvent used is selected from the group comprising of ether, dichloromethane, dichloroethane, ethyl acetate, petroleum ether and benzene.

14. A process as claimed in claim 1 wherein in step (xi), the organic solvent is stripped off at reduced pressure.

15. A process as claimed in claim 1 herein in step (xi), the crude product is distilled under vacuum.

16. A process as claimed in claim 1, wherein the bromobenzene thus obtained has boiling point in the range of 154–156° C.

17. A process as claimed in claim 1, wherein the yield of bromobenzene obtained is in the range of 50 to 90%.

* * * * *